(12) United States Patent
Michell et al.

(10) Patent No.: US 8,790,910 B2
(45) Date of Patent: Jul. 29, 2014

(54) LIVE VACCINE STRAIN

(71) Applicant: The Secretary of State for Defence, Salisbury (GB)

(72) Inventors: Stephen Lloyd Michell, Salisbury (GB); Petra Claire Farquhar Oyston, Salisbury (GB); Richard William Titball, Salisbury (GB)

(73) Assignee: The Secretary of State for Defence (GB)

( * ) Notice: Subject to any disclaimer, the term of this patent is extended or adjusted under 35 U.S.C. 154(b) by 0 days.

(21) Appl. No.: 13/673,233

(22) Filed: Nov. 9, 2012

(65) Prior Publication Data

US 2013/0122573 A1 May 16, 2013

Related U.S. Application Data

(62) Division of application No. 12/374,888, filed as application No. PCT/GB2007/002837 on Jul. 25, 2007, now Pat. No. 8,323,664.

(60) Provisional application No. 60/843,155, filed on Sep. 8, 2006.

(30) Foreign Application Priority Data

Jul. 25, 2006 (GB) .................................. 0614743.3

(51) Int. Cl.
*C12N 1/36* (2006.01)
*C12N 15/52* (2006.01)
*C12N 15/74* (2006.01)
*A61K 39/02* (2006.01)

(52) U.S. Cl.
USPC ..................... 435/252.3; 424/234.1; 536/23.1

(58) Field of Classification Search
USPC ..................... 424/234.1; 435/252.1; 536/23.1
See application file for complete search history.

(56) References Cited

U.S. PATENT DOCUMENTS

| | | | |
|---|---|---|---|
| 3,148,120 A | 9/1964 | Otto | |
| 4,235,871 A | 11/1980 | Papahadjopoulos et al. | |
| 4,235,877 A | 11/1980 | Fullerton | |
| 4,501,728 A | 2/1985 | Geho et al. | |
| 4,837,028 A | 6/1989 | Allen | |
| 4,912,094 A | 3/1990 | Myers et al. | |
| 5,019,369 A | 5/1991 | Presant et al. | |
| 5,066,596 A | 11/1991 | Manning et al. | |
| 5,187,074 A | 2/1993 | Treiber et al. | |
| 5,192,668 A | 3/1993 | Treiber et al. | |
| 5,278,302 A | 1/1994 | Caruthers et al. | |
| 5,308,854 A | 5/1994 | Hoffman, Jr. et al. | |
| 5,413,999 A | 5/1995 | Vacca et al. | |
| 5,476,874 A | 12/1995 | Hungate et al. | |
| 5,502,060 A | 3/1996 | Thompson et al. | |
| 5,578,597 A | 11/1996 | Spector et al. | |
| 5,663,169 A | 9/1997 | Young et al. | |
| 5,666,153 A | 9/1997 | Copeland | |
| 5,703,055 A | 12/1997 | Felgner et al. | |
| 5,846,978 A | 12/1998 | Coburn et al. | |
| 5,951,987 A | 9/1999 | Cherwonogrodzky et al. | |
| 6,261,568 B1 | 7/2001 | Gicquel et al. | |
| 6,268,171 B1 | 7/2001 | Meyer et al. | |
| 6,303,347 B1 | 10/2001 | Johnson et al. | |
| 6,350,454 B1 | 2/2002 | Thune | |
| 6,406,705 B1 | 6/2002 | Davis et al. | |
| 6,444,210 B1 | 9/2002 | Kournikakis et al. | |
| 6,444,445 B2 | 9/2002 | Nikolich et al. | |
| 6,444,804 B1 | 9/2002 | Lam et al. | |
| 6,544,518 B1 | 4/2003 | Friede et al. | |
| 6,552,006 B2 | 4/2003 | Raz et al. | |
| 6,558,670 B1 | 5/2003 | Friede et al. | |
| 6,764,840 B2 | 7/2004 | Johnson et al. | |
| 7,399,756 B2 | 7/2008 | Jomaa et al. | |
| 7,588,744 B1 | 9/2009 | Sylvester | |
| 7,592,326 B2 | 9/2009 | Karaolis | |
| 8,198,430 B2 | 6/2012 | Prior et al. | |
| 8,323,664 B2 | 12/2012 | Mitchell et al. | |
| 8,609,108 B2 | 12/2013 | Le Butt et al. | |
| 2001/0024653 A1 | 9/2001 | Gicquel et al. | |
| 2003/0022226 A1 | 1/2003 | Hooper et al. | |
| 2004/0087555 A1 | 5/2004 | Belmant et al. | |

(Continued)

FOREIGN PATENT DOCUMENTS

| | | |
|---|---|---|
| EP | 0250614 | 1/1988 |
| EP | 0362278 | 4/1990 |

(Continued)

OTHER PUBLICATIONS

*Francisella tularensis*, Poster presented at ASM Meeting, Baltimore, MD, Mar. 20-23, 2005, 11 pgs.
Genbank Accession No. AASP01000000.1, *Francisella tularensis* subsp. holarctica FSC200, whole genome shotgun sequence, Jan. 17, 2007.
Search Report dated Aug. 7, 2009 in Application No. GB0906234.0.
Tularemia, MedlinePlus Medical Encyclopedia. Located at http://www.nlm.nih.gov/medlineplus/ency/article/000856.htm, Jun. 28, 2011, 3 pages.

(Continued)

*Primary Examiner* — Padma V Baskar
(74) *Attorney, Agent, or Firm* — Kilpatrick Townsend & Stockton LLP; Dean W. Russell; Elena S. Polovnikova

(57) ABSTRACT

A strain of *Francisella* species wherein a gene which encodes for part of the glutamate metabolic pathway has been inactivated, and which is able to produce a protective immune response in an animal, for use as live prophylactic or therapeutic vaccine against infection by said *Francisella* species. Particularly effective strains include those where the capB gene is deleted. Other embodiments of the invention describe strains which compromise a further genetic mutation wherein a gene which encodes for another component of the cell is also inactivated. Pharmaceutical compositions comprising said strains, together with methods which utilize such strains are also described and claimed.

11 Claims, 8 Drawing Sheets

(56) References Cited

U.S. PATENT DOCUMENTS

| | | | |
|---|---|---|---|
| 2006/0280759 | A1 | 12/2006 | Titball et al. |
| 2007/0066801 | A1 | 3/2007 | Engler et al. |
| 2007/0128225 | A1 | 6/2007 | Prior et al. |
| 2007/0264233 | A1 | 11/2007 | Michell et al. |
| 2007/0292386 | A9 | 12/2007 | Campbell et al. |
| 2008/0207568 | A1 | 8/2008 | Belmant |
| 2009/0087456 | A1 | 4/2009 | Eyles et al. |
| 2009/0196887 | A1 | 8/2009 | Morita et al. |
| 2010/0021501 | A1 | 1/2010 | Michell et al. |
| 2010/0047283 | A1 | 2/2010 | Michell et al. |
| 2010/0080828 | A1 | 4/2010 | Prior et al. |
| 2010/0119524 | A1 | 5/2010 | Ulaeto et al. |
| 2010/0204184 | A1 | 8/2010 | Montero et al. |
| 2012/0082698 | A1 | 4/2012 | Conlan et al. |
| 2012/0107360 | A1 | 5/2012 | Le Butt et al. |
| 2013/0122573 | A1 | 5/2013 | Mitchell et al. |

FOREIGN PATENT DOCUMENTS

| | | |
|---|---|---|
| EP | 0109942 | 3/1991 |
| EP | 468520 | 1/1992 |
| EP | 671948 | 8/1997 |
| EP | 689454 | 10/1997 |
| EP | 2123285 | 11/2009 |
| GB | 2220211 | 1/1990 |
| GB | 2321103 | 7/1998 |
| GB | 0625587 | 12/2007 |
| GB | 2445028 | 6/2008 |
| GB | 0906234.0 | 4/2009 |
| GB | 2469565 | 10/2010 |
| RU | 2240822 | 4/2004 |
| WO | 8808430 | 11/1988 |
| WO | 8809797 | 12/1988 |
| WO | 9111172 | 8/1991 |
| WO | 9213871 | 1/1992 |
| WO | 9311791 | 6/1993 |
| WO | 9402518 | 2/1994 |
| WO | 9421292 | 9/1994 |
| WO | 9514026 | 5/1995 |
| WO | 9517210 | 5/1995 |
| WO | 9526204 | 10/1995 |
| WO | 9633739 | 10/1996 |
| WO | 9741234 | 11/1997 |
| WO | 9815287 | 4/1998 |
| WO | 9850399 | 11/1998 |
| WO | 9855148 | 12/1998 |
| WO | 9856414 | 12/1998 |
| WO | 9964301 | 12/1999 |
| WO | 0000462 | 1/2000 |
| WO | 0126683 | 4/2001 |
| WO | 0146127 | 6/2001 |
| WO | 0158485 | 8/2001 |
| WO | 0218600 | 3/2002 |
| WO | 02060935 | 8/2002 |
| WO | 03068151 | 8/2003 |
| WO | 03102191 | 12/2003 |
| WO | 2004004654 | 1/2004 |
| WO | 2004084935 | 10/2004 |
| WO | 2004098491 | 11/2004 |
| WO | 2005013918 | 2/2005 |
| WO | 2005021708 | 3/2005 |
| WO | 2005054258 | 6/2005 |
| WO | 2005063802 | 7/2005 |
| WO | 2006067635 | 6/2006 |
| WO | 2006103568 | 10/2006 |
| WO | 2006111019 | 10/2006 |
| WO | 2006131752 | 12/2006 |
| WO | 2007028985 | 3/2007 |
| WO | 2007034166 | 3/2007 |
| WO | 2007097789 | 8/2007 |
| WO | 2008012538 | 1/2008 |
| WO | 2008075075 | 6/2008 |
| WO | 2010086617 | 8/2010 |
| WO | 2010119245 | 10/2010 |

OTHER PUBLICATIONS

Agarwal et al., Antisense therapeutics: is it as simple as complementary base recognition, Molecular Medicine Today, 6, 2000, 72-81.

Agarwal et al., Medicinal chemistry and therapeutic potential of CpG DNA, Abstract Only, Trends in Mol. Med., 2002, 8: 114-121.

Alkhuder et al., Glutathione Provides a Source of Cysteine Essential for Intracellular Multiplication of *Francisella tularensis*, PLoS Pathogens, 2009, 5, 1-11.

Altschul et al., Basic local alignment search tool, Journal of Molecular Biology, vol. 215, No. 3, Oct. 5, 1990, pp. 403-410.

Altschul et al., Gapped BLAST and PSI-BLAST: a new generation of protein database search programs, Nucleic Acids Research, 1997, 25(17), 3389-3402.

Ascher et al., Modulation of delayed-type hypersensitivity and cellular immunity to microbial vaccines: effects of cyclophosphamide on the immune response to tularemia vaccine, Clin. Exp. Immunology, 1980, 41, pp. 225-226.

Ascher et al., Modulation of Delayed-Type Hypersensitivity and Cellular Immunity to Microbial Vaccines; Effects of Cyclophosphamide on the Immune Response to Tularemia Vaccine, Infection and Immunity, 1977, 18(2), 318-323.

Atkins et al., Characterisation of an acapsular mutant of *Burkholderia pseudomallei* identified by signature tagged mutagenesis, Journal Medical Microbiology, vol. 51, No. 7, Jul. 2002, pp. 539-547.

ATLAS Handbook of Microbiological Media, Thayer-Martin Agar, Modified; erd Ed., CRC Press, FLA, 2004, 1365-1369.

Barker et al., Basis for the Failure of *Francisella tularensis* Lipopolysaccharide to prime human Polymorphonuclear leukocyte, Infection and Immunity, 2006, 74(6), 3277-3284.

Bélanger et al., Functional analysis of genes responsible for the synthesis of the B-band O-antigen of *Pseudomonas aeruginosa* serotype 06 lipopolysaccharide, Microbiology, 1999, 145:3505-3521.

Bosio et al., Active suppression of the pulmonary immune response by *Francisella tularensis* Schu4, Journal of Immunology, vol. 178, Issue 7, Apr. 1, 2007, pp. 4538-4547.

Bowie et al., Deciphering the message in protein sequences: tolerance to amino acid substitutions, Science. Mar. 16, 1990;247(4948):1306-10, Mar. 16, 1990, pp. 1306-1310.

Broekhuijsen et al., Genome-Wide DNA Microarray Analysis of *Francisella tularensis* Strains Demonstrates Extensive Genetic Conservation within the Species but Identifies Regions that are Unique to the Highly Virulent *F. tularensis* subsp. tularensis, Journal of Clinical Microbiology, 41(7), Jul. 2003, pp. 2924-2931.

Buchele et al., Studies on pathogenesis and immunity in tularemia II. Immune Response of the white rat to bacterium tularense, Journal of Immunology, 63(2), 1949, pp. 135-145.

Burke Immunization Against Tularemia Analysis of the Effectiveness of Live *Francisella tularensis* Vaccine in Prevention of Laboratory Acquired Tularemia, Journal of Infectious Diseases, 135(1), Jan. 1977, pp. 55-60.

Burrows et al., Molecular characterization of the *Pseudomonas aeruginosa* serotype 05 (PA01) B-band lipopolysaccharide gene cluster, Molecular Microbiology, 22(3), 1996, 16 Pages.

Candela et al., Poly-gamma-glutamate in bacteria, Molecular Microbiology, 2006, 60(5): 1091-1098.

Carlsson et al., Enzyme-Linked Immunosorbent Assay for Immunological Diagnosis of Human Tularemia, Journal of Clinical Microbiology, vol. 10, No. 5, Nov. 1979, pp. 615-621.

Casetti et al., Drug-Induced Expansion and Differentiation of Vy9Vo2 T Cells in Vivo: The role of exogenous IL-2, Journal of Immunology, 2005, 1593-1599.

Chain et al., Complete genome sequence of *Francisella tularensis* LVS (Live Vaccine Strain), NCBI Reference Sequence: NC_007880.1, Jan. 25, 2012.

Chamberlain, Evaluation of Live Tularemia Vaccine Prepared in a Chemically Defined Medium, Applied Microbiology, 1965, 13(2):232-235.

Champion et al., Comparative genomic characterisation of *Francisella tularensis* starains, pLoS Pathogens, 2009, 5:e1000459.

(56) References Cited

OTHER PUBLICATIONS

Chart Lipopolysaccharide : Isolation and Characterization, in: Raton B, Arbor A (eds.) Methods in Practical Laboratory Bacteriology, CRC Press, London, Tokyo, 1994, 11-20.
Chen et al., Tularemia in BALB/c and C57BU6 mice vaccinated with *Francisella tularensis* LVS and challenged intradermally, or by aerosol with virulent isolates of pathogen: protection varies depending on pathogen virulence, route of exposure, host genetic background, Vaccine, 2003, 21: 3690-3700.
Clemens et al., Virulent and Avirulent Strains of *Francisella tularensis* Prevent Acidifcation and Maturation of Their Phagosomes and Escape Into the Cytoplasm in Human Macrophages, Infection and Immunity, 2004, 72(6):3204-3217.
Conlan et al., Different host defences are required to protect mice from primary systemis vs pulmonary infection with the faculative intracellular bacterial pathogen, *Francisella tularensis* LVS, Microb. Pathog., 2002, 32:127-134.
Conlan Vaccines against *Francisella tularensis*—past, present and future, Expert Rev. Vaccines, 2004, 3(3): 307-314.
Cowley et al., Isolation and characterization of *Francisella novicida* mutants defective in lipopolysaccharide biosynthesis, FEMS Microbiol Lett., 2000, 182:63-67.
Dalsgaard Saponin Adjuvants, 1974, 243-254.
Database Kegg [Online] Glutamate metabolism-*Francisella tularensis* subsp. tularensis SCHU S4, XP002468730, Retrieved from http://www.genome.jp/KEGG/Pathway/FTU/FTU00251.HTML, Feb. 19, 2007.
Davis et al., Pathology of Experimental Pneumonic Plague Produced by Fraction-1 Positive and Fraction-1 Negative *Yersinia pestis* in Agrican Green Monkeys (*Cercopithecus aethiops*), Arch. Pathol. Lab. Med, 1996, 120(2):156-163.
Deng et al., Identification of *Francisella tularensis* genes affected by iron limitation Infect., Immun., 2006, 74: 4224-4236.
Drabick et al., Analysis of Active Live Immunization Versus Passive Humoral Immunotherapy Against Attenuated and Virulent Strains of *Francisella tularensis*, Vaccine Research, 1997, 6(2): 67-74.
Drabick et al., Passive Protection of Mice against Lethal *Francisella tularensis* (Live Tularemia Vaccine Strain) Infection by the sera of human recipients of the Live Tularemia Vaccine, The American Journal of the Medical Sciences, 1994, 308:83-87.
Dreisbach et al., Purified Lipopolysaccharide from *Francisella tularensis* Live Vaccine Strain (LVS) Induces Protective Immunity against LVS Infection That Requires B Cells and Gamma Interferon, Infection and Immunity, 2000, 68:1988-1996.
Dunstan et al., Comparison of the Abilities of Different Attenuated *Salmonella typhimurium* Strains to Elicit Humoral Immune Responses against a Heterologous Antigen, Infection and Immunity, 1998, 66(2): 732-740.
Eigelsbach et al., Murine Model for Study of Cell-Mediated Immunity: Protection Against Death from Fully Virulent *Francisella tularensis* Infection, Infection & Immunity, 1975, 12(5): 999-1005.
Eigelsbach et al., Prophylactic effectiveness of live and killed tularemia vaccines, I.production of vaccine and evaluation in the white mouse and guinea pig, Journal of Immunology, 1961, 87: 415-425.
Ellis et al., Tularemia, Clinical Microbiology Reviews, 2002, 15(4): 631-646.
EMBL—Bank Sequence Database Accession No. AF140738, Jan. 19, 2000.
Eyles et al., Protection afforded against aerosol challenge by systemic immunisation with inactivated *Francisella tularensis* live vaccine strain (LVS), Microbial Pathogenesis, 2008, 44: 164-168.
Florence et al., 'Formulation' in vol. 5 of Comprehensive Medicinal Chemistry, Corwin Hansch; Chairman of Editorial Board, Pergamon Press, 1990, 567-591.
Forest et al., Type IV pili structure, assembly adn immunodominance: applications to vaccine design, Vaccines, 1997, 97:167-173.
Forslund et al., Direct repeat-mediated deletion of a type IV pilin gene results in major virulence attenuation of *Francisella tularensis*, Molecular Microbiology, 2006, 59(6):1818-1830.
Forslund et al., Type IV Pili is Required for Virulence of *Francisella tularensis*, American Society of Microbiology Biodefense Research meeting, Mar. 2005.
Fulop et al., Production and Characterization of Monoclonal Antibodies Directed against the Lipopolysaccharide of *Francisella tulzrensis*, Journal of Clinical Microbiology 29, 1991, 1407-12.
Fulop et al., Role of antibody to lipopolysaccharide in protection against low- and high high virulence, Vaccine 19, 2001, 4465-72.
Fulop et al., Role of lipopolysaccharide and a major outer membrane protein from *Francisella tularensis* in the induction of immunity against tularaemia, Vaccine 13(13), 1995, 1220-5.
Fulop et al., Role of two outer membrane antigens in the induction of protective immunity against *Francisella tularensis* strains of different virulence, FEMS Immunology and Medical Microbiology, vol. 13, 1996, 245-7.
GB10000743 Search Report, Aug. 3, 2011.
GB1006165.3 Search Report, Aug. 13, 2010.
GB2003/002338 Search Report dated Nov. 3, 2003 in International Application No. PCT/GB2003/002338, dated Nov. 3, 2003.
Gil et al., Presence of Pili on the Surface of *Francisella tularensis*, Infection and Immunity, 2004, 3042-3047.
Golovliov et al., A method for allelic replacement in *Francisella tularensis*, FEMS Microbiology Letters, vol. 222, 2003, 8 Pages.
Golovliov et al., Adjuvanticity of ISCOMs incorporating a T cell-reactive lipoprotein of the facultative intracelluar pathogen *Francisella tularensis*, Vaccine, vol. 13, No. 3, 1995, 7 Pages.
Golovliov et al., Indentification of proteins of *Francisella tularensis* induced during growth in macrophages and cloning of the gene encoding a prominently induced 23-kilodalton protein, Infection and Immunity, vol. 65, No. 6, Jun. 1997, 8 Pages.
Gossman et al., Quantitative Structure-Activity Relations of yo T Cell Activation by Phosphoantigens, Journal of Med. Chem., 2002, 45:4868-4874.
Gray et al., The identification of five genetic loci of *Francisella novicida* associated with intracellular growth, FEMS Microbiology Letters, 2002, 215: 53-56.
Green et al., Efficacy of the live attenuated *Francisella tularensis* vaccine (LVS) in a murine model of disease, Vaccine, 2005, 23: 2680-2686.
Greenspan et al., Defining Epitopes: It's not as easy as it seems, Nature Biotechnology, 1999, 17:936-937.
Groisman How bacteria resist killing by host—defense peptides, Trends Microbiol, 1994, 2:444-449.
Hahn et al., The type-4 pilus is the major virulence-associated adhesin of *Pseudomonas aeruginosa*—a review, Gene, 1997, 99-108.
Hartley et al., Grey variants of the line vaccine strain of *Francisella tularensis* lack lipopolysaccharide O-antigen, show reduced ability to survive in macrophages and do not induce protective immunity in mice, Vaccine, 24:989-996, 2006.
Hartmann et al., Delineation of a CpG Phosphorothioate Oligodeoxynucleotide for Activating Primate Immune Responses in Vitro and in Vivo, Immunology, 2000, 164: 1617-1624.
Hatch et al., Immunogenic Substances in culture filtrates and lysates of *Pasteurella tularensis*, Journal of Bacteriology, Sep. 1964, vol. 88(3), 566-573.
Hertle et al., Dual-function vaccine for *Pseudomonas aeruginosa*: characterization of a chimeric exotoxin A-pilin protein, Infection and Immunity, 2001, 69(11):6962-6969.
Hollis et al., *Francisella philomiragia* comb. Nov. (Formerly *Yersinia philomiragia*) and *Francisella tularensis* Biogroup Novicida(Formerly *Francisella novicida*) Associated with Human Disease, Journal of Clinical Microbiology, 1989, 27(7):1601-1608.
Hooper et al., DNA vaccination with Vaccinia Virus L1R and A33R Genes Protects Mice against a Lethal Poxvirus Challenge, Virology, 2000, 266: 329-339.
Hubalek et al., Comparative proteome analysis of cellular proteins extracted from highly virulent *Francisella tularensis* ssp. tularensis and less virulent *F. tularensis* ssp. holarctica and *F. tularensis* ssp. mediaasiatica, Proteomics, 2004, 4:3048-3060.
Huseby et al., Practical points regarding routine determination of—glutamyl transferase (-GT) in serum with a kinetic method at 37oC., Scandinavian Journal Clin. Lab. Invest., 34:357-363, 1974.

(56) References Cited

OTHER PUBLICATIONS

Isherwood et al., Vaccination strategies for *Francisella tularensis*, Advanced Drug Delivery Reviews, 2005, 57(9): 1403-1414.
Johansson et al., Worldwide Genetic Relationships among *Francisella tularensis* Isolates Determined by Multiple-Locus Variable-Number Tandem Repeat Analysis, Journal of Bacteriology, 186(17):5808-5818, 2004.
Johnson et al., Routes of Administration and Dosage Regimes, Comprehensive Medicinal Chemistry, 1990, 5:593-613.
Kadzhaev et al., Identification of genes contributing to the virulence of *Francisella tularensis* SCHU S4 in a mouse intradermal infection model, PLoS One, 4(5), 2009, e5463.
Karlsson et al., Sequencing of the *Francisella tularensis* Strain Schu 4 Genome Reveals the Shikimate and Purine Metabolic Pathways, Targets for the Construction of a Rationally Attenuated Auxotrophic Vaccine, Microbial & Comparative Genomics, 2000, 5(1): 25-39.
Kawula et al., Use of Transposon-Transposase Complexes to Create Stable Insertion Mutant Strains of *Francisella tularensis* LVS, Applied and Environmental Microbiology, 2004, 70:6901-6904.
Kenne et al., Bacterial Polysaccharides, The Polysaccharides, Molecular Biology, 1983, vol. 2, pp. 287-362.
Khlebnikov et al., Outer Membrance of a lipopolysaccharide-protein comples (LPS-17 KdA Protein) as chemical tularemia vaccines, FEMS Immunology and Medical Microbiology, 1996, 13:227-33.
Kieffer et al., *Francisella novicida* LPS has greater immunobiological activity in mice than *F. tularensis* LPS, and contributes to *F. novicida* murine pathogenesis, Microbes and Infection, 2003, 5:397-403.
Kiss et al., Characterization of fig operon mutants of *Francisella novicida* U112, FEMS Micriobiol Letters, 2008, 270-277.
Knirel et al., Somatic antigens of *Pseudomonas aeruginosa*, Eur. J. Biochem., 1985, 150:541-550.
Koskela et al., Cell-mediated immunity against *Francisella tularensis* after natural infection, Scandinavian Journal of Infectious Diseases, 1980, 12(4): 281-287.
Kuolee et al., Vaccines and therapeutic agents for tularemia, Informa Healthcare, 2007, 267-275.
Kus et al., Significant differences in type IV pilin allele distribution among *Pseudomonas aeruginosa* isolates from cystic fibrosis (CF) versus non-CF patients, Microbiology, 2004, 150:1315-1326.
Laemmli Cleavage of structural Proteins during the Assembly of the Head of Bacteriophage T4, Nature, 1970, 227, pp. 680-685.
Lai et al., Expression of IgIC is necessary for intracellular growth and induction of apoptosis in murine macrophages by *Francisella tularensis*, Microbial Pathogenesis, 2004, 37:225-230.
Larsson et al., Molecular evolutionary consequences of niche restriction in *Francisella tularensis*, PLoS Pathoges, 2009, 5:e1000472.
Larsson et al., The complete genome sequence of *Francisella tularensis*, the causative agent of tularemia, Nature Genetics, 2005, 37(2): 153-159.
Lascola et al., Rapid comparative genomic analysis for clinical microbiology, Genome Res, 2008, 18:742-750.
Lauriano et al., MgIA regulates transcription of virulence factors necessary for *Francisella tularensis* intraamoebae and intramacrophage survival, Proc. Natl. Acad. Sci. USA, 2004, 101:4246-4249.
Lavine et al., Immunization with heat-killed *Francisella tularensis* LVS elicits protective antibody-mediated immunity, Eur. J . Immunology, 2007, 37: 3007-3020.
Law et al., Antibody Neutralization of the Extracellular Enveloped Form of Vaccinia Virus, Virology, 2001, 280: 132-142.
Lipman et al., Rapid and Sensitive Protein Similiarity Searches, Science, 1985, 227: 1435-1441.
Mack et al., A new cell Assay to Determine the Virulence of *Francisella tularensis*, Letters in Applied Microbiology, 1994, 19:158-160.
Maier et al., In Vivo Himarll-Based Transposon Mutagenesis of *Francisella tularensis*, Applied Environmental Microbiology, 2006, 72(3):1878-1885.
Mann et al., Rationally designed tularemia vaccines, Expert Rev Vaccines, 2009, 8(7): 877-885.
McCrumb et al., Aerosol Infection of Man with *Pasteurella tularensis*, Bacteriol Rev., 25(3):262-7, 1961.
McLendon et al., *Francisella tularensis*: Taxonomy, Genetics, and Immunopathogenesis of a Potential Agent of Biowarfare, Annual Rev. Microbiology, 2006, 60:167-185.
McMurry et al., Diversity of *Francisella tularenis* Schu4 antigens recognized by T lymphocytes after natural infections in humans: identification of candidate epitopes for inclusion in a rationally designed tularemia vaccine, Vaccine, 2007, 25(16):3179-91.
Michell et al., A capB mutant of *Francisella tularensis*, URL:http://www.sgm.ac.uk/meetings/pdfabstracts/keele2005abs.pdf (2008), Sep. 12, 2005.
Mitchell et al., Development of real-time PCR assays for the specific detection of *Francisella tularensis* ssp. Tularensis, holartica and mediaasiaatica, Molecular and Cellular Probes, 2010, 24:72-76.
Nano et al., A *Francisella tularensis* Pathogenicity Island Required for Intramacrophage Growtn, Journal of Bacteriology, 2004, 186(19):6430-6436.
Narayanan et al., Immunotherapy of Tularemia: Characterisation of a monoclonal antibody reactive with *Francisella tularensis*, Journal of Leukocyte Biology, 1993, 53:112-116.
Nielsen et al., Peptide nucleic acids (PNAs): Potential anti-sense and anti-gene agents, Anti-Cancer Drug Des., 1993, 8:53-63.
Nutter et al., Antigens of *Pasteurella tularensis*: Preparative Procedures, Applied Microbiology, Jul. 1971, vol. 22(1), 44-48.
O'Hagan Recent developments in vaccine delivery systems, Current Drug Targets, Infectious Disorders, Bentham Science Publishers, Hilversum, NL, 2001, 1(3): 273-286.
Olsufiev et al., Comparative study of strains of *B. Tularense* in the old and New World and thereir Taxonomy, J. Hyg. Epidemiol. Microbiol. Immunol., 1959, 3:138-149.
Ormsbee et al., Studies on *Bacterium tularense* Antigens I. The Isolation, Purification and Biologic Activity of Antigen Preparations from *Bacterium tularense*, Journal of Immunology, 1954, 74:351-358.
Ormsbee et al., Studies on *Bacterium tularense* Antigens, I. Chemical and Physical Characteristics of Protective Antigen Preparations, Journal of Immunology, 1954, 74(5):359-370.
Overholt et al., An analysis of forty-two cases of laboratory-acquired tularemia. Treatment with broad spectrum antibiotics, The American Journal of Medicine, 1961, 30: 785-806.
Oyston et al., Tularemia vaccine: past, present and future, Antonie van Leeuwenhoek, 2005, 87:277-281.
Pammit et al., Intranasal vaccination with a defined attenuated *Francisella novicida* strain induces gamma interferon-dependent antibody-mediated protection against tularemia., Infect. Immun.vol. 74, No. 2, Apr. 2006, 2063-2071.
Pavlov et al., Cryptic plasmid pFNL10 from *Francisella novicida*-like F6168: the base of plasmid vectors for *Francisella tularensis*, FEMS Immunology and Medical Microbiology, vol. 13, 1996, pp. 4.
Pechous et al., A *Francisella tularensis* Schu S4 Purine Auxotroph is Highly Attenuated in Mice but Offers Limited Protection Against Homologous Intranasal Challenge, PLoS ONE, 2008, 3(6):1-10.
Pechous et al., Construction and Characterization of an Attenuated Purine Auxotroph in a *Francisella tularensis* Live Vaccine Strain, Infection and Immunity, 2006, 74(8):4452-4461.
Petrosino et al., Chromosome rearrangement and diversification of *Francisella tularensis* revealed by the type B (OSU18) genome sequence, J. Bacteriol, 2006, 188(19):6977-85.
Petrovsky et al., Freeing vaccine adjuvants from dangerous immunological dogma, Expert Rev . Vaccines, 2008, 7(1):7-10.
Petrovsky et al., New-Age Vaccine Adjuvants: Friend or Foe?, BioPharmInternational.com., Aug. 2, 2007, 12 pgs.
Poquet et al., Expansion of Vy9Vo2 T Cells Is Triggererd by *Francisella tularensis*-Derived Phosphoantigens in Tularemia but Not after Tularemia Vaccination, Infection and Immunity, 1998, 66(5):2107-2114.
Prior et al., Preliminary analysis an annotation of the partial genome sequence of *Francisella tularensis* strain Schu 4, Journal of Applied Microbiology, 2001, 91: 614-620.

(56) References Cited

OTHER PUBLICATIONS

Qin et al., Identification of an essential *Francisella tularensis* subsp. tularensis Virulence Factor, Infection and Immunity, 2009, 152-161.
Qin et al., Identification of transposon insertion mutants of *Francisella tularensis* tularensis strain Schu S4 deficient in intracellular replication in the hepatic cell line HepG2, BMC Microbiology, 2006, 6:69.
Quarry et al., A *Francisella tularensis* subspecies novicida purF mutant, but not a purA mutant, induces protective immunity to tularemia in mice, Vaccine 25, 2007, 2011-8.
Ramakrishnan in Abstracts of the 104th ASM General Meeting, New Orleans, LA, abstract # D-178, May 25, 2004.
Reed et al., A Simple Method of Estimating Fifty Per Cent Endpoints, Am. J. Hygiene, 1938, 27(3):493-497.
Reyrat et al., Counterselectable Markers: Untapped Tools for Bacterial Genetics and Pathogenesis, Infection and Immunology, 66(9), 1998, pp. 4011-4017.
Richards et al., Identification of *Francisella* genes up-regulated in the macrophage, Poster at the International Conference on tularemia, Nov. 2006, 7 pages.
Robertson et al., Detection of the Osmoregulator Betaine in Methanogens, Applied and Environmental Microbiology, 1990, 56:1504-1508.
Robertson et al., β-Aminoglutaric acid is a major soluble component of *Methanococcus thermolithotrophicus*, Biochimica et Biophysica Acta, 1989, 992:320-326.
Rohmer et al., Comparison of *Francisella tularensis* genomes reveals evolutionary events, Genome Biol, 2007, 8:R102.
Rohmer et al., Potential source of *Francisella tularensis* live vaccine strain attenuation determined by genome comparison, Infectious Immunology, 2006, 74(12):6895-6906.
Roper et al., Extracellular Vaccine Virus Envelope Glycoprotein Encoded by the A33R Gene, Journal of Virology, 1996, 70(6):3753-3762.
Russell et al., The efficacy of ciprofloxacin and doxycycline against experimental ularaemia, J. Antimicrob. Chemother., 1998, 41:461-5.
Salomonsson et al., A Role for a Type IV Pilus in Virulence of *Francisella tularensis*, American Society for Microbiology Meeting, 2005.
Salomonsson et al., A Role for a Type IV Pilus in Virulence of *Francisella tularensis*, Society of General Microbiology, 155th Meeting, Sep. 2004.
Salyers et al., Vaccines and Other Approaches to Modulating the Immune Response, Bacterial Pathogenesis a Molecular Approach, 1994, 90.
Sambrook et al., Molecular Cloning, Molecular Cloning: A laboratory Manual, 2001, 3rd ed., Spring Harbor laboratory New York, NY, 2001, v-xx.
Samrakandi et al., Genome diversity among regional populations of *Francisella tularensis* subspecies, FEMS Microbiology Letters, 2004, 237:9-17.
Sandstrom et al., A Capsule-Deficient Mutant of *Francisella tularensis* LVS Exhibits Enhanced Sensitivity to Killing by Serum but Dimished Sensitivity to Killing by Polymorphonuclear Leukocytes, Infection and Immunity, 56(5), 1988, 9 Pages.
Sandstrom et al., Antigen from *Francisella tularensis*: Nonidentity Between Determinants Participating in Cell-Mediated and Humoral Reactions, Infect. Immun., 1984, 12(1):101-106.
Sandstrom The Tularaemia Vaccine, J. Chem. Tech. Biotechnology, 1994, 59:315-320.
Sanger et al., DNA sequencing with chain-terminating inhibitors, Proc. Natl. Acad. Sci. USA, 1977, 74:5463-5467.
Shen et al., Mice sublethally infected with *Francisella novicida* U112 develop only marginal protective immunity against systemic or aerosol challenge with virulent type A or B strains of *F. tularensis*, Microbial Pathogenesis, 2004, 37:107-110.

Simon et al., A broad host range mobilisation system for in vitro genetic engineering: transposon mutagenesis in Gram-negative bacteria, Biotechnology, 1:784-791, 1983.
Sonnhammer et al., A hidden Markov model for predicting transmembrane helicesinprotein sequences, In: Glasgow S, Littlejohn T et al. (eds.), 1998, 175-182.
Sorokin et al., *Francisella tularensis* resistance to bactericidal action of normal human serum, FEMS Immunology and Medical Microbiology, 1996, 13:249-252.
Su et al., Genome-Wide Identification of *Francisella tularensis* Virulence Determinants, Infection and Immunity, 2007, 3089-3101.
Sullivan et al., Characterization of the Siderophore of *Francisella tularensis* and Role of fsIA in Siderophore production, Journal of Bacteriology, 2006, 188:3785-3795.
Svensson et al., Evolution of Subspecies of *Francisella tularensist*, Journal of Bacteriology, vol. 187, Jun. 2005, 5 Pages.
Szoka Comparative Properties and Methods of Preparation of Lipid Vesicles (Liposomes), Ann. Rev. Biophy. Bioeng., 9:467-508, 1980, 467-508.
Tarnvik et al., Nature of Protective Immunity to *Francisella tularensis*, Review of Infectious Diseases, 1989, 11(3):440-451.
Tarnvik et al., Orchestration of the protective immune response to intracellular bacteria: *Francisella*, FEMS Immunology and Medical Microbiology, 1996, 13(3):221-225.
Tarnvik et al., Stimulation of Human Lymphocytes by a Vaccine Strain of *Francisella tularensis*, Infection and Immunity, 1975, 12(5):951-957.
Tarnvik et al., Stimulation of Subpopulations of Human Lymphocytes by a Vaccine Strain of *Francisella*, Infection and Immunity, 1978, 20(3):698-704.
Tempel et al., Attenuated *Francisella novicida* Transposon Mutants Protect Mice against Wild-Type Challenge, Infection and Immunity, 2006, 74(9):5095-5105.
Tigertt Soviet viable *Pasteurella tularensis* vaccines, Bacteriol. Rev. 26:354-373, 1962.
Titball et al., Will the enigma of *Francisella tularensis* virulence soon be resolved?, Trends in Microbiology, 2003, 11(3):118-123.
Tonjum et al., The pilus colonization factor of pathogenic neisserial species: organelle biogenesis and structure/function relationships—a review, Gene, 1997, 155-163.
Twine et al., A Mutant of *Francisella tularensis* Strain SCHU S4 Lacking the Ability to Express a 58-Kilodalton Protein Is Attenuated for Virulence and is an Effective Live Vaccine, Infection and Immunity, 2005, 73(12):8345-8352.
Vinogradov et al., Structural Analysis of *Francisella tularensis* lipopolysaccharide, European Journal of Biochemistry, 269(24), Dec. 2002, 7 Pages.
Vogel et al., Acetylornithinaase of *Escherichia coli*: Partial Purification and some Properties, J. Biol. Chem., 1955, 218:97-106.
Waag et al., Cell-Mediated and humoral immune responses after vaccination of human volunteers with the live vaccine strain of *Francisella tularensis*, Clin. Diagn. Lab. Immunol, 1995, 2:143-148.
Waag et al., Immunogenicity of a new lot of *Francisella tularensis* live vaccine strain in human volunteers, FEMS Immunol. Med. Microbiol., 1996, 13:205-209.
Waldo et al., Proteome Cataloging and relative quantification of *Francisella tularensis* strain Schu4 in 2D PAGE using preparative isoelectric focusing, Journal of Proteome Research, 6(9), 2007, 3484-90.
Weiner The immunobiology and clinical potential of immunostimulatory CpG oligodeoxynucleotides, Journal of Leukocyte Biology, 2000, 68:456-463.
Westphal et al., Bacterial Lipopolysaccharides, Methods in Carbohydrate Chemistry, Ed. Roy L. Whistler, Academic Press, 1965, 5: 83-91.
Whitfield et al., Modulation of the surface architecture of gram-negative bacteria by the action of surface polymer:Lipid A-core ligas and by determinants of polymer chain length, Mol.Micro., 1997, 23(4):629-638.
Yamamoto et al., Ability of oligonucleotides with certain palindromes to induce interferon production and augment natural killer cell activity is associated with their base length, Antisense Res Dev. 1994 Summer;4(2):119-22., 1994, 119-22.

(56) References Cited

OTHER PUBLICATIONS

Zhao et al., Effect of different chemically modified oligodeoxynucleotides on immune stimulation, Biochemical Pharmacology, 51, 1996, 173-82.
Office Action dated Jul. 1, 2011 in U.S. Appl. No. 12/374,888.
Office Action Response dated Dec. 8, 2011 in U.S. Appl. No. 12/374,888.
Office Action dated Apr. 4, 2012 in U.S. Appl. No. 12/374,888.
Office Action Response dated Jul. 5, 2012 in U.S. Appl. No. 12/374,888.
Notice of Allowance dated Aug. 1, 2012 in U.S. Appl. No. 12/374,888.

Figure 1

Genomic arrangement of capB locus in wildtype F. tularensis SchuS4

Percent survival vs Days

- SchuS4ΔcapB 1.6x10$^6$ cfu
- SchuS4ΔcapB 1.6x10$^5$ cfu
- SchuS4ΔcapB 1.6x10$^4$ cfu
- naïve controls All mice challenged with 70cfu SchuS4

Figure 8:
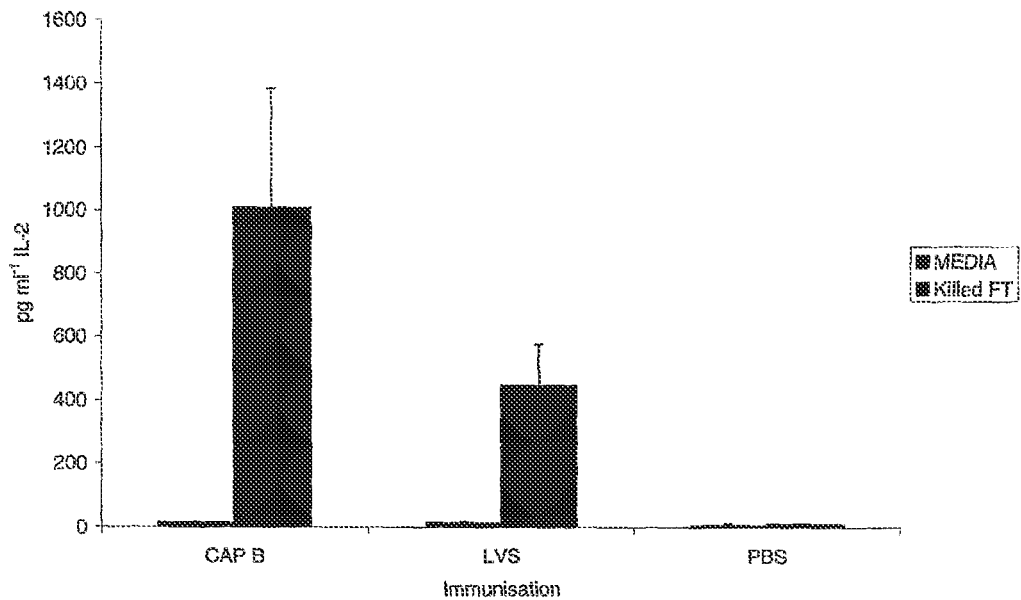
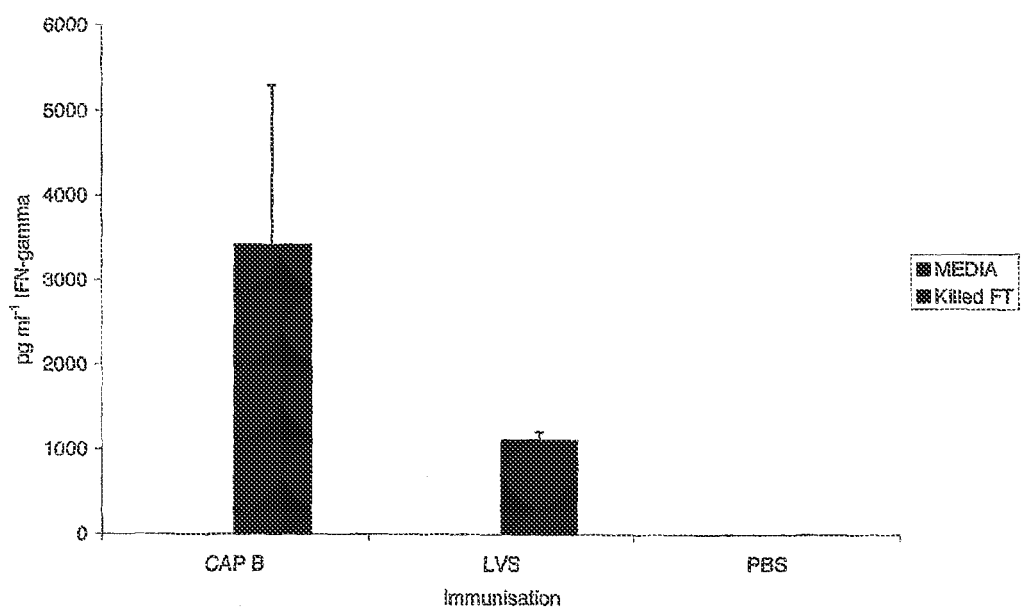

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 1
ctgacgcgta ggcagtgtgg ttatgggtag                              30

<210> SEQ ID NO 2
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 2
gacggtaacc caaatacgac gacaattaac                              30

<210> SEQ ID NO 3
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 3
ctgggtaacc tccagcaaac tcttatattc                              30

<210> SEQ ID NO 4
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 4
tagacgcgta cccaatcaac ccagtacaag                              30

<210> SEQ ID NO 5
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 5
gctggttacc taagaggttc caactttcac                              30

<210> SEQ ID NO 6
<211> LENGTH: 30
<212> TYPE: DNA
<213> ORGANISM: Artificial sequence
```

```
<220> FEATURE:
<223> OTHER INFORMATION: Synthetic sequence: Primer

<400> SEQUENCE: 6
ctaggttacc tttaagggca ccaataactg                                    30
```

LIVE VACCINE STRAIN

CROSS REFERENCE TO RELATED APPLICATIONS

This application is a divisional of U.S. patent application Ser. No. 12/374,888 flied on Mar. 5, 2009, now U.S. Pat. No. 8,323,664 which is the U.S. national phase of International Application No. PCT/GB2007/002837 filed on Jul. 25, 2007, and published in English on Jan. 31, 2008, as International Publication No. WO 2008/012538 A2, which application claims priority to Great Britain Application No. 0614743.3 filed on Jul. 25, 2006 and U.S. Provisional Application Ser. No. 60/843,155 filed on Sep. 8, 2006, the entire contents of all of which are incorporated herein in their entireties by reference.

This invention relates to live strains of *Francisella* species, their use as prophylactic or therapeutic vaccines, to compositions comprising these strains, and their use in the prevention or treatment of bacterial infection. *Francisella tularensis* is an extremely pathogenic Gram-negative bacterium and is the etiological agent of the zoonotic disease Tularemia. There are four recognized sub-species of *F. tularensis*, including subspecies *tularensis, holarctica*, and *novicida*, which exhibit a high degree of genetic conservation. The most virulent subspecies is *Francisella tularensis* subspecies *tularensis*, which has an infectious dose in humans of as little as 10 cells via the airbourne route.

At present there is no available vaccine against *F. tularensis* infection although it has been demonstrated previously that an undefined attenuated strain of *Francisella tularensis*, which has been designated *Francisella tularensis* live vaccine strain (LVS), is capable of providing protection against the most virulent subspecies, *tularensis*. However, the LVS vaccine is not registered and has only been used to vaccinate at-risk individuals under special license. This license has now been withdrawn. The LVS strain is likely to remain unlicensed because the genetic changes that are responsible for the attenuating phenotype are not understood at the molecular level. Therefore, there exists a possibility that the vaccine strain could revert back to the fully virulent form. Further, it has been shown that whilst LVS provides effective protection in the mouse model of infection, protection is not complete. The protection afforded by LVS against an aerosol challenge of the most virulent *tularensis* subspecies is sub-optimal. Clearly, a vaccine which is genetically stable and which provides complete protection is highly desirable.

The fact that naturally occurring, attenuated strains of *F. tularensis* can induce protective immunity does suggest that an attenuated strain with properly defined genetic mutations in the organism's virulence factors is a feasible approach in vaccine development. Unfortunately, however, relatively little is known about the virulence mechanisms of *F. tularensis* and, as such, virulence factors have proven to be very difficult to predict; the recent completion of the genome sequence of the virulent strain *F. tularensis* subspecies *tularensis* SchuS4 has so far failed to reveal the presence of classical virulence factors such as toxins or type-III secretion systems, which are predominant in so many other pathogenic bacteria.

Some efforts to identify new vaccine strains have focused on naturally occurring strains (other than LVS) or on spontaneously attenuated strains of *F. tularensis*, such as the FSC043 mutant of SchuS4 reported by Twine et al (*Infection and Immunity* Vol 73, 2005, pp8345-8352). Examination of these attenuated mutants has confirmed that mutations can lead to attenuated strains which afford some level of protection against tularemia. However, the molecular basis of this attenuation and protection is unknown and, in any case, the protection afforded is not better than that provided by LVS. The problem remains, therefore to find defined mutations which give complete protection against the most virulent forms of *Francisella*.

A live vaccine strain of *Francisella* derived from the subspecies *novicida*, which contains a single genetic mutation, is described in co-pending International Application number PCT/GB2004/001264, the contents of which are hereby incorporated by reference. This application shows that a genetic lesion in the purine enzyme pathway provides attenuated strains which are also protective in the mouse model of infection. Whilst this clearly represents a significant advance in the development of a vaccine for tularemia, it is widely recognized that an additional genetic mutation would be required to enable such a strain to obtain licensed status. The problem remains, therefore, to determine further mutations which result in attenuated strains but which also provide complete protection against all strains of *Francisella tularensis*.

New live vaccines, containing well defined mutations and which are fully protective against tularemia are therefore required.

The applicants have found that by modifying strains of *Francisella* in a particular way, attenuated strains which are protective can be produced. These live strains can be used as the basis for new vaccines against tularemia.

The present invention therefore provides a strain of *Francisella* species wherein a gene which encodes for part of the glutamate metabolic pathway has been inactivated, and which is able to produce a protective immune response in an animal, for use as a live prophylactic or therapeutic vaccine against infection by said *Francisella* species.

As used herein, the term "metabolic pathway" means the sum total of the chemical processes occurring in a cell, in which the processes occur in steps, through which compounds are gradually built up or broken down. Each step of the metabolic pathway is catalysed by an enzyme, whose structure is encoded by a gene.

As used herein the term "glutamate metabolic pathway" means the chemical processes whereby glutamate is synthesised or broken down, including those steps wherein an enzyme catalyses the formation of glutamate or catalyses the use of glutamate to form another material.

Thus, genes that encode for part of the metabolic pathway in *Francisella* species include those genes which encode for the formation of glutamate and those which encode for enzymes which are utilised in the glutamate metabolic pathway. Inactivation of such a gene is likely to interrupt the normal metabolic pathway such that, for example, glutamate is not produced by the cell or that the amount of glutamate produced is significantly altered when compared with the virulent *Francisella* species, such as *Francisella tularensis* subspecies *tularensis* SchuS4, in which the same gene having been inactivated.

The presence, or absence, of glutamate (or aminoglutaric acid) may be readily determined using 13C, 15N or 1H Nuclear Magnetic Resonance Spectroscopy (NMR), as described by the papers by Robertson, D. E. et al (*Applied and Environmental Microbiology* 1990, vol. 56 pp1504-1508 and *Biochimica at Biophysica Acta* 1989, vol. 992,pp320-326) and the quantities of glutamate produced by strains of the present invention may be readily determined using techniques such as Liquid Chromatography-Mass Spectrometry (LC-MS), which are routine in the art.

As used herein "glutamate" refers to the amino acid glutamate or glutamic acid, which may exist in the form of β-glutamate (beta-glutamate) or γ-glutamate (gamma-glutamate).

The inventors have found that inactivating a gene which encodes for part of the glutamate metabolic pathway provides a strain which is both attenuated and protective against exposure to virulent *Francisella* species. Without wishing to be bound by theory, it is thought that part of the glutamate metabolic pathway may include, or have an effect on the formation of extracellular capsule. Thus, genes which encode for the synthesis of capsule, or which are analogous to these genes when compared with established capsule encoding genes from other organisms, may fall within the definition of genes that encode for part of the metabolic pathway, as described above.

As used herein, the term "capsule" means an extracellular component, commonly a layer, of polysaccharide and/or protein which protects a bacterial cell and which, in association with pathogenic bacteria, serves as a barrier against phagocytosis by the white blood cells of an animal host, in which the pathogenic bacteria are present.

As used herein, the term "capsule-encoding gene" means a gene which encodes for a protein, or other molecule, which is involved in the synthesis of the capsule component of a bacterial cell or a gene which is homologous to a gene which has been assigned as having some involvement in bacterial capsule biosynthesis, including involvement in the synthesis of capsule or any component thereof and involvement in the assembly and/or transport of said components to form a capsular structure.

As used herein, the terms "homologous" and "homology" means, at the protein level, the similarity of two amino acid sequences are such that the two sequences share greater than 30% identity. Identity in this instance can be judged for example using the BLAST program (vs. 2.2.12) found at http://www.ncbi.nim.nih.gov/BLAST/ or the algorithm of Lipman-Pearson with, for example, Ktuple:2, gap penalty:4, Gap Length Penalty:12, standard PAM scoring matrix or other suitable parameters as readily determined by a person skilled in the art (Lipman, D. J. and Pearson, W. R., Rapid and Sensitive Protein Similarity Searches, *Science*, 1985, vol. 227, 1435-1441).

Genes which encode for the glutamate metabolic pathway (including those which encode for a capsule component) of the *Francisella* bacterium may be determined by analysis of the relevant genome sequence and/or by comparison with other bacteria which have well-defined capsule encoding genes.

Gene inactivation can be carried out using any of the conventional methods known in the art. Typically, the strain is transformed with a vector which has the effect of down-regulating or otherwise inactivating the gene. This can be done by mutating control elements such as promoters and the like which control gene expression, by mutating the coding region of gene so that any product expressed is inactive, or by deleting the gene entirely. Alternatively, the gene can be inactivated at the RNA or protein level, by transforming the cell so that it expresses a sense or anti-sense construct which binds to DNA or RNA encoding the gene to prevent transcription thereof.

Preferably however, the gene is inactivated by complete or partial deletion mutation or by insertional mutation.

Specifically, the applicants have found that it is preferable to inactivate one or more of the genes which has been annotated in the *Francisella tularensis* genome as being a capsule-encoding gene, for example capB or capC (hereinafter "cap-genes). In particular the applicants have found that it is preferable to inactivate a cap gene in *Francisella* species such as *F. tularensis* subspecies *tularensis* or subspecies *holarctica*. In a preferred embodiment, the capB gene (FTT0805) and/or the capC gene (FTT0806) of *F. tularensis* subspecies *tularensis* is inactivated to provide one strain according to the present invention. In other embodiments, the corresponding genes of other *Francisella* species are deleted to provide other strains according to the preset invention. The corresponding cap genes from other *Francisella* species will usually have at least 80%, preferably at least 85% homology and more preferably at least 90% homology to, and similar function to, the cap genes of *F. tularensis* subspecies *tularensis*. In a more preferred embodiment, the capB gene (F1T0805) of *F. tularensis* subspecies *tularensis* strain SchuS4 is inactivated to provide a preferred strain.

In particular, the applicants have found that a strain of *Francisella tularensis* which has a cap gene inactivated is attenuated and is protective against challenge from virulent *Francisella* species. As illustrated hereinafter, a strain of *F. tularensis* subspecies *tularensis* which has an inactivated cap gene is protective in mice. In particular the applicants have shown that deletion of the capB gene from *F. tularensis* subspecies *tularensis* SchuS4 strain provides an attenuated strain which is protective against aerosol challenge with the virulent SchuS4 strain.

The strain of the invention suitably has a further defined mutation or lesion so as to reduce the risk of the bacterium reverting to a virulent form. In this case, the mutation is in a gene which is selected so that the strain is suitably attenuated, but can still retain the ability to stimulate a sufficient immune response to provide long term protection. Suitable additional mutations can be identified using conventional methods, and examination and analysis of the current live vaccine strain (LVS) or other attenuated strains may assist in the identification. Examples of these mutations include, but are not limited to, mutations to the FTT0918 and FTT0919 genes. Alternatively the further defined mutation may advantageously involve a gene which encodes for another component of the cell, which is not part of the glutamate metabolic pathway. Such further mutations include, but are not limited to, mutations which inactivate pilin genes, for example mutations to pilA and/or pilE and/or pilC genes or other mutations such as those described in co-pending British patent application number GB0511722.1 (the contents of which are hereby incorporated by reference), mutations which inactivate genes which encode enzymes in the purine pathway, for example mutations to purA and/or purF genes and other purine pathway genes such as those described in co-pending international Application number PCT/GB2004/001264 (the contents of which are hereby incorporated by reference).

Particular preferred examples of further defined mutations are inactivation of the purF and/or inactivation of the pilA gene and/or inactivation of the FTT0918 gene.

It will be understood by the skilled person that such further defined mutations can be achieved by using any conventional method as hereinbefore described but that in preferred embodiments of the inventions the gene which encodes for other components of the cell is inactivated by complete or partial deletion mutation or by insertional mutation.

Since the strains of the present invention have been found to be protective against infection by *Francisella* species in the mouse model of infection, the strains also provide useful vaccines against the diseases caused by *Francisella* infections and in particular, tularemia. It is therefore preferred that the strains are formulated into pharmaceutical compositions, in which they are combined with a pharmaceutically acceptable carrier. Such pharmaceutical compositions form a second aspect of the invention.

Suitable carriers may be solid or liquid carriers as is understood in the art. They may suitably be formulated for administration to mucosal surfaces (for example for oral use, of for administration by inhalation or insufflation) or for parenteral administration.

In particular they are formulated as sterile aqueous or oily solutions for intravenous, subcutaneous, intramuscular or intramuscular dosing.

Alternatively they are formulated for administration to mucosal surfaces and in particular for intranasal application. Such formulations may include microencapsulation of the strain in the composition, or microencapsulation of the entire composition. Such microencapsulation techniques are commonly known in the art.

Compositions are suitably prepared in unit dosage forms, as conventional in the art. They are administered at dosages which are determined using clinical practice, and depend upon factors such as the nature of the patient, the severity of the condition, and the precise vaccine strain being employed. Typically dosage units will comprise $10^5$-$10^8$ cfu. Dosages may be boosted as appropriate or necessary.

Compositions may also contain further immunogenic reagents which are effective against *F. tularensis* infection or other diseases. They may further contain other agents such as adjuvants and the like, which enhance the host's immune response to the vaccine.

In a further aspect the present invention relates to the use of a strain of *Francisella* species wherein a gene which encodes for part of the glutamate metabolic pathway has been inactivated, and which is able to produce a protective immune response in an animal, in the preparation of a live prophylactic or therapeutic vaccine against infection by *Francisella* species. In particular, such strains find use in the preparation, or manufacture, of a vaccine for the treatment of Tularaemia.

In yet a further aspect, the invention provides a method of preventing or treating infection caused by *Francisella* species, which method comprises administering to an animal, including a human being, an effective amount of a strain or of a pharmaceutical composition, each as hereinbefore described.

In particular, the method is useful in the treatment of infection caused by *Francisella tularensis* subspecies *tularensis*.

Novel strains which are suitable for vaccine use form a further aspect of the invention. In particular, the invention provides a strain of *Francisella* species wherein a gene which encodes for part of the glutamate metabolic pathway has been inactivated. In particular the strains which are suitable for use as vaccines are as hereinbefore described. In a preferred embodiment the inactivated gene is capB or capC. It is further preferred that the strain is a strain of *Francisella tularensis* subspecies *tularensis*, for example the SchuS4 strain.

The invention will now be particularly described by way of non-limiting Example, with reference to the accompanying diagrammatic drawings in which:

FIG. 1 shows the strategy for the construction of a suicide plasmid for the deletion of the capB gene from the *F. tularensis* subspecies *tularensis* strain SchuS4.

FIG. 4 shows survival data of BALB/c mice infected subcutaneously with wild type and capB mutant strains of *F. tularensis* subspecies *tularensis* strain SchuS4.

FIG. 5 shows survival data of BALB/c mice, administered with a capB mutant strain of *F. tularensis* subspecies *tularensis* strain SchuS4, and subsequently challenged with 70 mean lethal doses (MLD) of the virulent strain, *F. tularensis* subspecies *tularensis* strain SchuS4.

FIG. 8 shows a graph which quantifies the IL-2 and IFN-γ recall response of spleen cells harvested from mice immunized subcutaneously with 100 μl of PBS containing $10^4$ CFU *F. tularensis* subsp. *tularensis* strain SchuS4 ΔcapB, *F. tularensis* live vaccine strain (LVS) or PBS alone and then subsequently stimulated with wild type *F. tularensis* subsp. *tularensis* strain SchuS4.

EXAMPLE 1

Construction of a Plasmid containing a Mutated Allele of *F. tularensis*

The capB gene of *F. tularensis* subspecies *tularensis* strain SchuS4 encodes a protein of 405 amino acids (aa) that has 36% identity to the 397 as CAPB protein from *Bacillus anthracis* strain 'Ames Ancestors'. Regions of DNA flanking the capB gene of *F. tularensis* were PCR amplified from *F. tularensis* susbspecies *tularensis* strain SchuS4 using the primer pairs P1/P2 and P3/P4 as shown in Table 1. The chloramphenicol resistance cassette (Cam-r) was PCR amplified from the plasmid pKK202 with the primer pair CamF/CamR.

TABLE 1

Primers used for the construction of pSMP42-Sequences in bold indicate the sequence complementary to Francisella DNA and the underlined sites in the 5' extensions are restriction sites.

| P1 | 5'-CTG<u>ACGCGT</u>-AGGCAGTGTGGTTATGGGTAG-3' |
|---|---|
| P2 | 5'-GAC<u>GGTAACC</u>-CAAATACGACGACAATTAAC-3' |
| P3 | 5'-CTG<u>GGTAACC</u>-TCCAGCAAACTCTTATATTC-3' |
| P4 | 5'-TAG<u>ACGCGT</u>-ACCCAATCAACCCAGTACAAG-3' |
| CamF | 5'-GCT<u>GGTTACC</u>-TAAGAGGTTCCAACTTTCAC-3' |
| CamR | 5'-CTA<u>GGTTACC</u>-TTTAAGGGCACCAATAACTG-3' |

The left and right flanks and the chloramphenicol resistance cassette were assembled as shown in FIG. 1, and cloned into the suicide plasmid pSMP22 to give the construct pSMP42. This gave a plasmid-borne mutant allele that could be used for recombinational exchange with the wild type chromosomal allele.

EXAMPLE 2

Generation of a *F. tularensis* Strain deleted for capB

Figure 2:
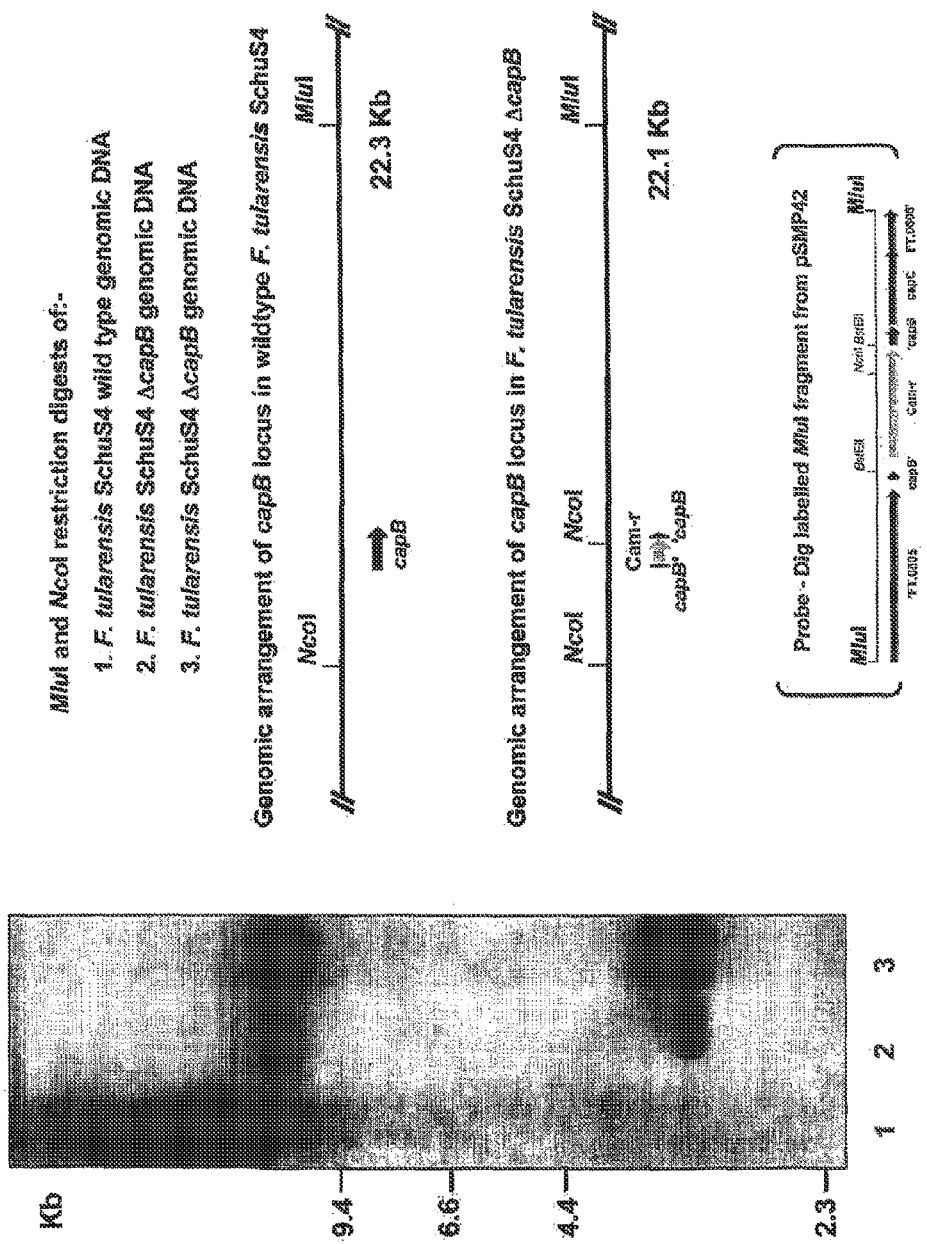
FIG. 2 shows a southern blot of genomic DNA from wild type and capB mutant strains of *F. tularensis* subspecies *tularensis* strain SchuS4.

The suicide plasmid pSMP42 was electroporated into the *E. coli* mobilising strain S-17 λpir. The plasmid was then introduced from the mobilising strain to *F. tularensis* subspecies *tularensis* strain SchuS4 by conjugal transfer. Transconjugants were selected on chloramphenicol and merodiploids arising from chromosomal integration of the suicide plasmid were resolved by plating on Thayer Martin agar containing sucrose at 5%. Allelic replacement mutants were confirmed by Southern blot analysis as shown in FIG. 2. Genomic DNA of wild type and capB deletion mutants (ΔcapB) of *F. tularensis* subspecies *tularensis* strain SchuS4 was digested with Mlul and Ncol, separated by agarose gel electrophoresis and transferred to a nylon membrane. The Mlul insert of pSMP42 was labelled with DIG-11-dUTP during PCR amplification with the primer pair P1/P4 and used as a probe to hybridise to the membrane. DNA fragments to which the probe hybridised were detected in a chemiluminescent assay (CSPD substrate, 30 min exposure, X-ray film). The ΔcapB mutant contained two hybridising fragments of 12.5 Kb and 3.2 Kb as shown in FIG. 2.

EXAMPLE 3

Comparison of Phenotype-effect of Osmotic Stress

Figure 3:
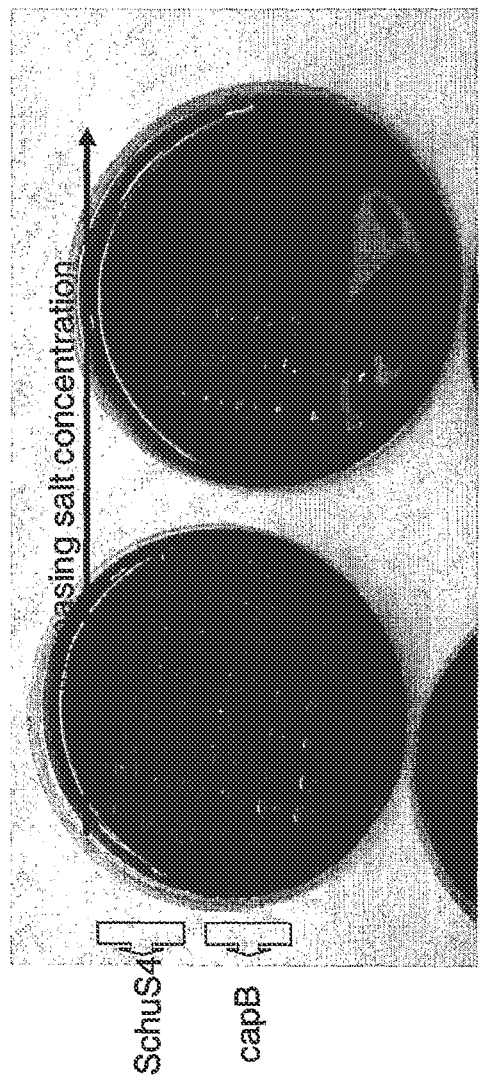
FIG. 3 shows the effects of osmotic stress on wild type *F. tularensis* subsp. *tularensis* strain SchuS4 and the ΔcapB mutant strain of the invention, when grown in a range of salt conditions.

*F. tularensis* subsp. *tularensis* strain SchuS4 Δcap8 *and F. tularensis* subsp. *tularensis* strain SchuS4 (wild type) were suspended in a range of salt (nacl) concentrations (up to 5 M) and then plated onto BCGA media using 20 μl droplets. Bacterial growth was assessed after 72 hours and the results are portrayed in FIG. 3. it was apparent that, as compared with the wild type, SchuS4 ΔcapB grew less efficiently at the highest salt (5 M) concentration. It appeared that ΔcapB was also more sensitive at the low salt concentrations. This indicates that the ΔcapB mutant has a different phenotype to wild type *F. tularensis* and exhibits different growth characteristics in osmotic environments.

EXAMPLE 4

Determination of Virulence of a capB Mutant in the Mouse Model of Tularemia

Figure 4:
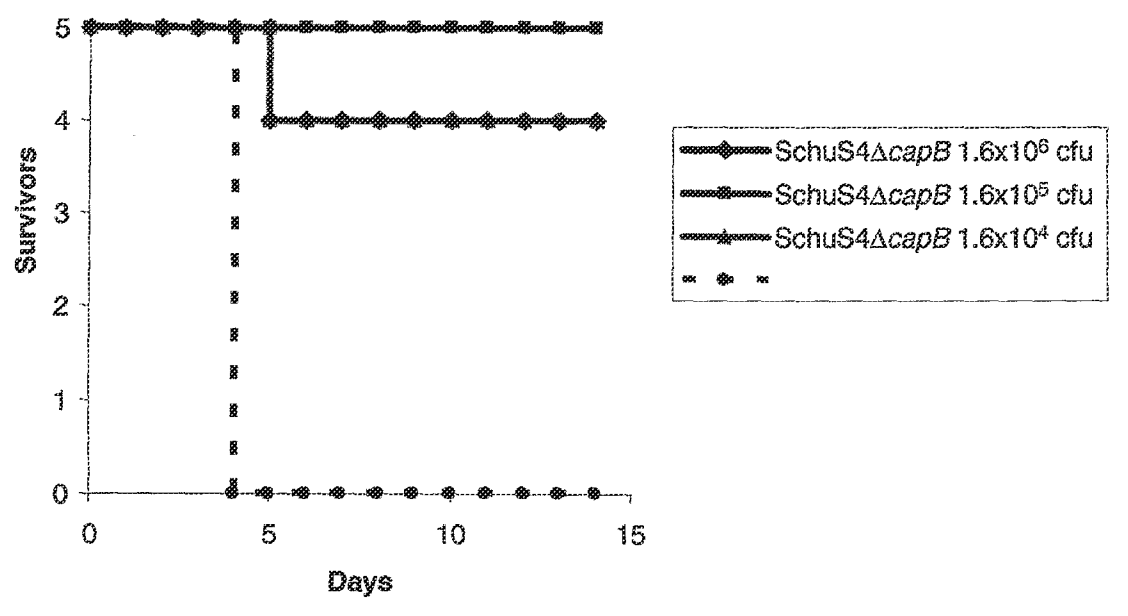

Several investigators have determined that the MLD of *F. tularensis* susbspecies *tularensis* is ~10 colony forming units (CFU) in the BALB\c mouse, irrespective of route of administration. In order to determine whether capB is required for virulence, groups of six female BALB\c mice, aged 6-8 weeks, were infected subcutaneously with wild-type SchuS4 and ΔcapB SchuS4 strains of *F. tularensis* subspecies *tularensis*. As previously reported mice infected with $10^2$ (115) CFU of SchuS4 succumbed to infection by day 5 post-infection. In contrast, 100% of the mice infected with $1.6 \times 10^5$ and 80% (4 out of 5) of mice infected with $1.6 \times 10^6$ and $1.6 \times 10^4$ CFU of the ΔcapB isogenic strain survived as shown in FIG. 4. This level of survival following deletion of a single gene demonstrates that capB is an important gene in the virulence of *F. tularensis* susbspecies *tularensis*.

EXAMPLE 5

Protection Afforded by a capB Mutant of *Francisella tularensis*

The chromosomal copy of the gene capB was deleted by allelic exchange as described in example 1 and 2. Genetic analysis was performed to ensure that the gene was removed (as per example 2) and a clonal population of the resultant strain was prepared. Upon subcutaneous administration to female Balb/c mice (6-8 weeks), $1.6 \times 10^5$ bacteria of the ΔcapB mutant strain failed to cause death in all five mice. This is in contrast to the parental wild-type strain of which only 115 bacteria were required to kill all 5 mice of a control group in 5 days. 46 days after immunisation with the capB negative strain, survivors of the infection detailed in Example 4 were challenged with 70 mean lethal doses (MLD) of a virulent strain of *F. tularensis* (SchuS4 strain). Non-immunised (naïve controls) mice succumbed to infection and died within 5 days whereas mice immunised with the capB mutant were protected and did not die as shown in FIG. 5.

EXAMPLE 6

Survival Against Virulent Challenge

Figure 6:
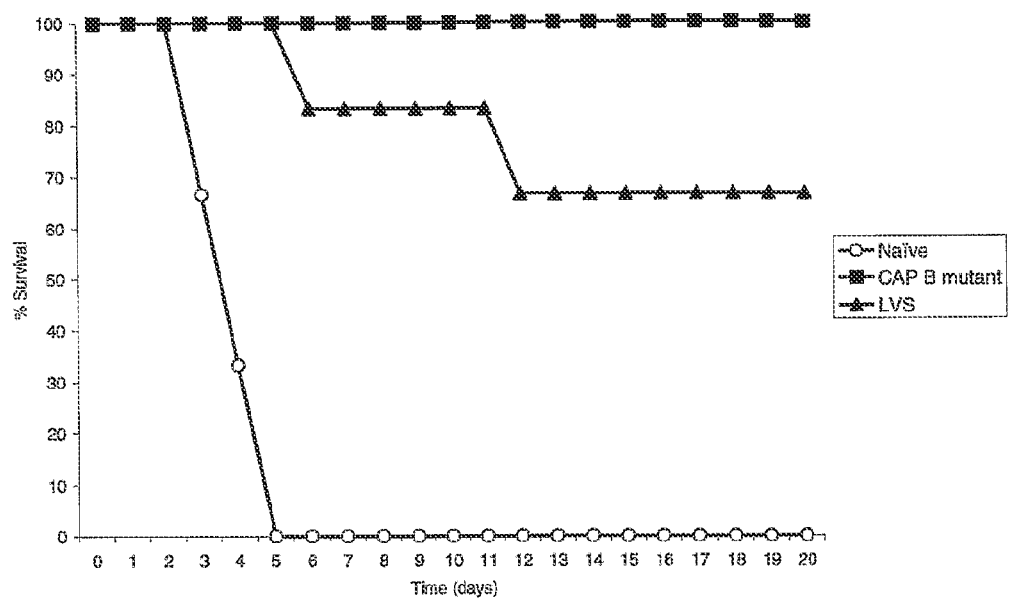
FIG. 6 shows survival data of Female BALB/c mice (6-8 weeks old), injected subcutaneously with 100 μl of PBS containing $10^4$ CFU *F. tularensis* subsp. *tularensis* strain SchuS4 ΔcapB, *F. tularensis* live vaccine strain (LVS) or PBS alone and eight weeks later challenged with $10^4$ CFU administered by the subcutaneous route.

Female BALB/c mice (6-8 weeks old) were injected subcutaneously with 100 μl of PBS containing $10^3$ CFU *F. tularensis* subsp. *tularensis* strain SchuS4 ΔcapB (prepared as described above), *F. tularensis* live vaccine strain (LVS) or PBS alone. Eight weeks later mice were challenged with $10^4$ CFU wild type *F. tularensis* subsp. *tularensis* strain SchuS4 administered by the subcutaneous route. Survival data, shown in FIG. 6, clearly indicates that superior protection is afforded by the capB deletion mutant than the live vaccine strain, and that 100% survival was observed.

EXAMPLE 7

Colonisation and Clearance in vivo of *F. tularensis* Strains

Figure 7:
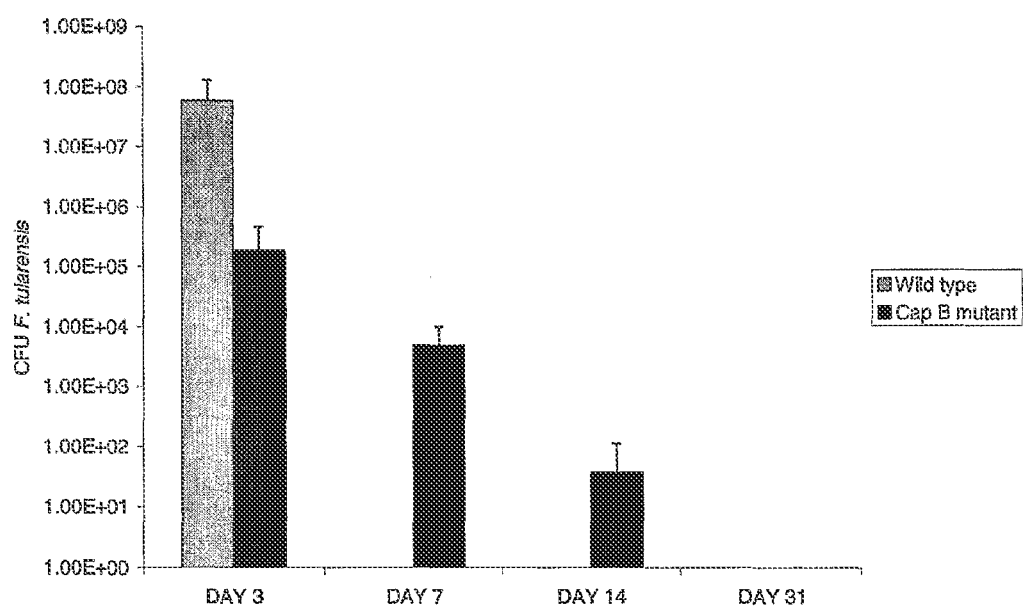
FIG. 7 shows a graph depicting the colonization and clearance of bacteria from the spleens of mice administered with either wild type *F. tularensis* subsp. *tularensis* strain SchuS4 or the ΔcapB mutant strain of the present invention.

Female BALB/c mice (6-8 weeks old) were injected subcutaneously with 100 μl of PBS containing $10^4$ CFU wild type *F. tularensis* subsp. *tularensis* strain SchuS4 or *F. tularensis* subsp. *tularensis* strain SchuS4 ΔcapB. Groups of 4 mice were killed 3, 7, 14 and 31 days following inoculation of the bacteria. Spleens were removed and the number of bacteria per spleen determined by serial dilution in PBS followed by microbiological culture on BCGA agar plates for 96 hours at 37 OC. None of the mice injected with wild type SchuS4 survived longer than five days post inoculation, which precluded determination of splenic bacterial burdens in these mice on days 7, 14 and 31 post inoculation. However, at day 3 post inoculation there was a highly significant ($P<0.001$) difference in the numbers of bacteria in the spleens of mice injected with wild type and the ΔcapB mutant; mice injected with *F. tularensis* subsp. *tularensis* strain SchuS4 ΔcapB had substantially lower numbers of bacteria in their spleens. Animals injected with *F. tularensis* subsp. *tularensis* strain SchuS4 ΔcapB steadily cleared the organism and no viable bacteria were detected in the spleens of these animals at 31 days post inoculation; indicating that they had effectively cleared the mutant. These results shown in FIG. 7 indicate that the capB mutant strain is less likely to cause latent infection after administration.

EXAMPLE 8

IL-2 and IFN-γ Recall Response of Mice Immunized with the capB Mutant Strain of Example Female BALB/c mice (6-8 weeks old) were injected subcutaneously with 100 μl of PBS containing $10^4$ CFU *F. tularensis* subsp. *tularensis* strain SchuS4 ΔcapB, *F. tularensis* live vaccine strain (LVS) or PBS alone. 40 days later groups of immunised 4 mice were killed and their spleens removed.

Single cell suspensions of spleen cells were prepared in culture media (RPMI-1640) (Sigma, UK) supplemented with 10% heat inactivated foetal bovine serum (FBS) (Sigma, UK); 1% penicillin/streptomycin glutamine (Sigma, UK) and 50 µM 2-mercaptoethanol (Sigma, UK). Cells were stimulated overnight in triplicate with either heat killed *F. tularensis* subsp. *tularensis* strain SchuS4 (5 µg ml$^{-1}$ protein) in supplemented RPMI 1640 or supplemented RPMI 1640 alone. Il-2 and IFN-γ secretion from the cells was determined using cytokine bead array technology (SD Biosciences, Oxford UK). As compared with mice injected with PBS, spleen cells from animals immunized with SchuS4 ΔcapB or LVS secreted significant quantities of IL-2 and IFN-γ when re-stimulated in vitro with inactivated *F. tularensis* strain SchuS4. However, when spleen cells from animals immunized with SchuS4 ΔcapB or LVS were cocultured with media alone, no significant IL-2 or IFN-γ secretion was detected. These results are shown in FIG. 8.

We claim:

1. An isolated strain of *Francisella tularensis*, subspecies *tularensis* or *holarctica*, wherein gene capB was inactivated by deletion.

2. The isolated strain of claim 1, wherein the isolated strain is a strain of *Francisella tularensis* subspecies *tularensis*.

3. The isolated strain of claim 1, wherein the isolated strain is a strain of *Francisella tularensis* subspecies *holarctica*.

4. The isolated strain of claim 1, wherein the isolated strain is a strain of *Francisella tularensis* subspecies *tularensis* SchuS4.

5. The strain of claim 1, wherein the isolated strain comprises an inactivated gene other than capB.

6. The isolated strain of claim 5, wherein the gene other than capB or is selected from the group consisting of FTT0918, FTT0919 and FTT1564.

7. The isolated strain of claim 5, wherein the gene other than capB or is a gene which encodes for a pilin subunit or is a gene which encodes for an enzyme in the purine pathway.

8. The isolated strain of claim 5, wherein the gene other than capB or is a gene selected from the group consisting of pilA, pilE, pilC, purA and purF.

9. The isolated strain of claim 1, wherein the isolated strain is able to stimulate an immune response to *Francisella tularensis* infection in an animal when administered to the animal.

10. A pharmaceutical composition comprising the isolated strain of claim 1.

11. A pharmaceutical composition comprising the isolated strain of claim 5.

* * * * *